US008626296B2

(12) United States Patent
Von Arx et al.

(10) Patent No.: US 8,626,296 B2
(45) Date of Patent: *Jan. 7, 2014

(54) METHOD AND APPARATUS OF ACOUSTIC COMMUNICATION FOR IMPLANTABLE MEDICAL DEVICE

(75) Inventors: Jeffrey A. Von Arx, Minneapolis, MN (US); Scott T. Mazar, Woodbury, MN (US); Abhijeet V. Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 28 days.

This patent is subject to a terminal disclaimer.

(21) Appl. No.: 13/453,406

(22) Filed: Apr. 23, 2012

(65) Prior Publication Data
US 2012/0209342 A1 Aug. 16, 2012

Related U.S. Application Data

(63) Continuation of application No. 12/322,497, filed on Feb. 3, 2009, now Pat. No. 8,165,677, which is a continuation of application No. 10/888,956, filed on Jul. 9, 2004, now Pat. No. 7,489,967.

(51) Int. Cl.
*A61N 1/372* (2006.01)

(52) U.S. Cl.
CPC ........... *A61N 1/37217* (2013.01); *A61N 1/3727* (2013.01)

USPC .......................................................... 607/32

(58) Field of Classification Search
USPC ........................................ 607/30–33, 59–61
See application file for complete search history.

(56) References Cited

U.S. PATENT DOCUMENTS

| 5,113,859 | A  | * | 5/1992  | Funke ............................... 607/4 |
| 6,236,889 | B1 | * | 5/2001  | Soykan et al. .................. 607/30 |
| 6,472,991 | B1 | * | 10/2002 | Schulman et al. ......... 340/995.1 |
| 8,165,677 | B2 | * | 4/2012  | Von Arx et al. ................ 607/32 |

* cited by examiner

*Primary Examiner* — Carl H Layno
*Assistant Examiner* — Jessica Sarcione
(74) *Attorney, Agent, or Firm* — Faegre Baker Daniels LLP

(57) ABSTRACT

An implantable medical device includes an acoustic transducer for intra-body communication with another medical device via an acoustic couple. The acoustic transducer includes one or more piezoelectric transducers. In one embodiment, an implantable medical device housing contains a cardiac rhythm management (CRM) device and an acoustic communication circuit. The acoustic communication circuit includes an error detection circuit configured for detecting an error rate associated with demodulated incoming acoustic signals and a frequency selection circuit configured for adjusting a carrier frequency of outbound acoustic signals. The acoustic transducer is electrically connected to the acoustic communication circuit to function as an acoustic coupler and physically fastened to a wall of the implantable housing, directly or via a supporting structure.

20 Claims, 11 Drawing Sheets

METHOD AND APPARATUS OF ACOUSTIC COMMUNICATION FOR IMPLANTABLE MEDICAL DEVICE

CROSS REFERENCE TO RELATED APPLICATIONS

This application is a continuation of U.S. application Ser. No. 12/322,497, filed Feb. 3, 2009, to issue as U.S. Pat. No. 8,165,677, which is a continuation of U.S. application Ser. No. 10/888,956, filed Jul. 9, 2004, now issued as U.S. Pat. No. 7,489,967, which are hereby incorporated by reference in their entirety for all purposes.

TECHNICAL FIELD

This document relates generally to implantable medical systems and particularly, but not by way of limitation, to an implantable medical device including an acoustic transducer for communications with another device by acoustic coupling.

BACKGROUND

Medical devices are implanted in human bodies for monitoring physiological conditions, diagnosing diseases, treating diseases, or restoring functions of organs or tissues. As one type of such implantable medical devices, an implantable CRM device monitors a patient's cardiac functions and/or treats cardiac arrhythmias, heart failure, and other cardiac disorders by delivering electrical and/or other therapies to the patient's cardiovascular system including the heart. One example of implantable CRM devices is implantable pacemakers. An implantable pacemaker delivers electrical pulses to the heart to restore cardiac rhythm and coordinate contractions in various cardiac regions, thereby improving hemodynamic performance. Another example of implantable CRM devices is implantable cardioverter/defibrillators (ICDs). ICDs deliver higher energy electrical stimuli to the heart to treat tachyarrhythmias including tachycardia and fibrillation. In addition to pacemakers and ICDs, examples of implantable CRM devices include, but are not limited to, implantable pacemaker/defibrillators that combine the functions of implantable pacemakers and ICDs, implantable drug delivery devices, and any other implantable devices for monitoring, diagnosing, and/or treating cardiac disorders.

Because an implantable CRM device is often intended for long-term use after being implanted in a patient, its size, complexity, and power consumption are inherently constrained. Consequently, a CRM system may include an external device or system and one or more implantable devices. The external device or system provides for a user interface for the CRM system and enables the CRM system to perform functions that the implantable CRM device alone is incapable of performing. Communication between an implantable CRM device and the external device or system is performed by telemetry through an inductive couple or a radio-frequency electromagnetic link. The CRM system may also perform certain functions by coordinated operation of the implantable CRM device and another one or more implantable devices. Such coordinated operation enables the CRM system to perform, for example, monitoring and/or therapeutic functions at multiple locations in a body that are practically difficult to access by using a single implantable device. For this and other reasons, there is a need for an intra-body communication link between two implantable medical devices.

SUMMARY

An implantable medical device includes an acoustic transducer for intra-body communication with another medical device via an acoustic couple. The acoustic transducer includes one or more piezoelectric transducers physically fastened to the housing of the implantable medical device, directly or via a supporting structure.

In one embodiment, an implantable medical device includes a CRM device, an acoustic communication circuit, an acoustic transducer, and an implantable housing. The acoustic communication circuit is coupled to the CRM device and includes at least one of a data transmitter and a data receiver. The acoustic transducer is coupled to the acoustic communication circuit and functions as an acoustic coupler for acoustic communication. The implantable housing includes a wall forming a chamber to contain the CRM device and the acoustic communication circuit.

In one embodiment, an implantable medical device includes a sensing and/or therapy delivery circuit, a plurality of acoustic transducers, an acoustic communication circuit, and an implantable housing. The acoustic transducers function as an acoustic coupler for acoustic communication. The acoustic communication circuit is coupled to the sensing and/or therapy delivery circuit and includes a transducer interface circuit coupled to the acoustic transducers. The implantable housing includes a wall forming a chamber to contain the sensing and/or therapy delivery circuit and the acoustic communication circuit.

In one embodiment, a CRM system includes two or more medical devices. One medical device is an implantable medical device including a CRM device, an acoustic communication circuit coupled to the CRM device, and an acoustic transducer coupled to the acoustic communication circuit. The acoustic transducer functions as an acoustic coupler for an acoustic couple. Another medical device communicates with the implantable medical device via the acoustic couple.

In one embodiment, an implantable medical device includes an acoustic communication circuit, an acoustic transducer, and an implantable housing. The acoustic transducer is coupled to the acoustic communication circuit and functions as an acoustic coupler for acoustic communication. The implantable housing includes a wall forming a chamber to contain at least the acoustic communication circuit. The acoustic transducer is fastened to the wall of the implantable housing. In an alternative embodiment, a diaphragm is connected to the wall of the implantable housing. The acoustic transducer is fastened to the diaphragm.

In one embodiment, an implantable medical device is to be communicatively coupled to a first and second medical device and includes a CRM device, an acoustic transducer, and an acoustic communication circuit. An implantable housing contains the CRM device and the acoustic communication circuit. The acoustic transducer is fastened to the implantable housing to be an acoustic coupler for acoustic communication between the implantable medical device and the second medical device. The acoustic communication circuit includes a data receiver circuit, a data transmitter circuit, and a frequency selection circuit. The data receiver circuit receives and demodulates a first incoming acoustic signal and a second incoming acoustic signal and includes an error detector. The first incoming acoustic signal includes a first carrier signal modulated by incoming data and the second incoming acoustic signal includes a second carrier signal modulated by incoming data. The error detector detects an error rate of each demodulated incoming acoustic signal. The data transmitter circuit modulates and transmits an a first outgoing acoustic signal and a second outgoing acoustic signal and includes a variable-frequency waveform generator. The first and second outgoing acoustic signals include includes a first and a second carrier signal, respectively, modulated by outgoing data. The variable-frequency waveform generator generates the first and second carrier signals with programmable carrier frequencies. The frequency selection circuit adjusts the each carrier frequency based on the error rate.

In one embodiment, a method for an implantable medical device to communicate with a second medical device is provided. An incoming acoustic signal including a first carrier signal modulated by incoming data is received from the second medical device. The incoming acoustic signal is demodulated. An error rate of the demodulated incoming acoustic signal is detected. A second carrier signal having a programmable carrier frequency is generated. The second carrier signal is modulated with the outgoing data. An outgoing acoustic signal including the modulated second carrier signal is translated to the second medical device. The carrier frequency is adjusted using the error rate.

A method for making an implantable medical device with acoustic communication is provided. In one embodiment, a CRM device with a communication circuit is provided. An implantable housing including a wall forming a chamber is provided. An acoustic transducer is connected to the communication circuit to function as an acoustic coupler. An acoustic coupler assembly including the acoustic transducer is connected to the wall. The CRM device and the communications circuit are encapsulated in the chamber of the implantable medical device.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this document are not necessarily to the same embodiment, and such references contemplate more than one embodiment.

This document discusses, among other things, an implantable medical device including an acoustic communication circuit for intra-body acoustic communication. The intra-body acoustic communication is performed between two implantable medical devices or between one implantable medical device and one external medical device attached onto the skin. The implantable medical device of the present subject matter is described in this document by using an implantable CRM device as a specific example. However, it is to be understood that the present methods and apparatuses may be employed in other types of implantable medical devices, including, but not being limited to, neural stimulators, neuromuscular stimulators, drug delivery devices, and various types of other therapeutic and monitoring devices.

Figure 1:
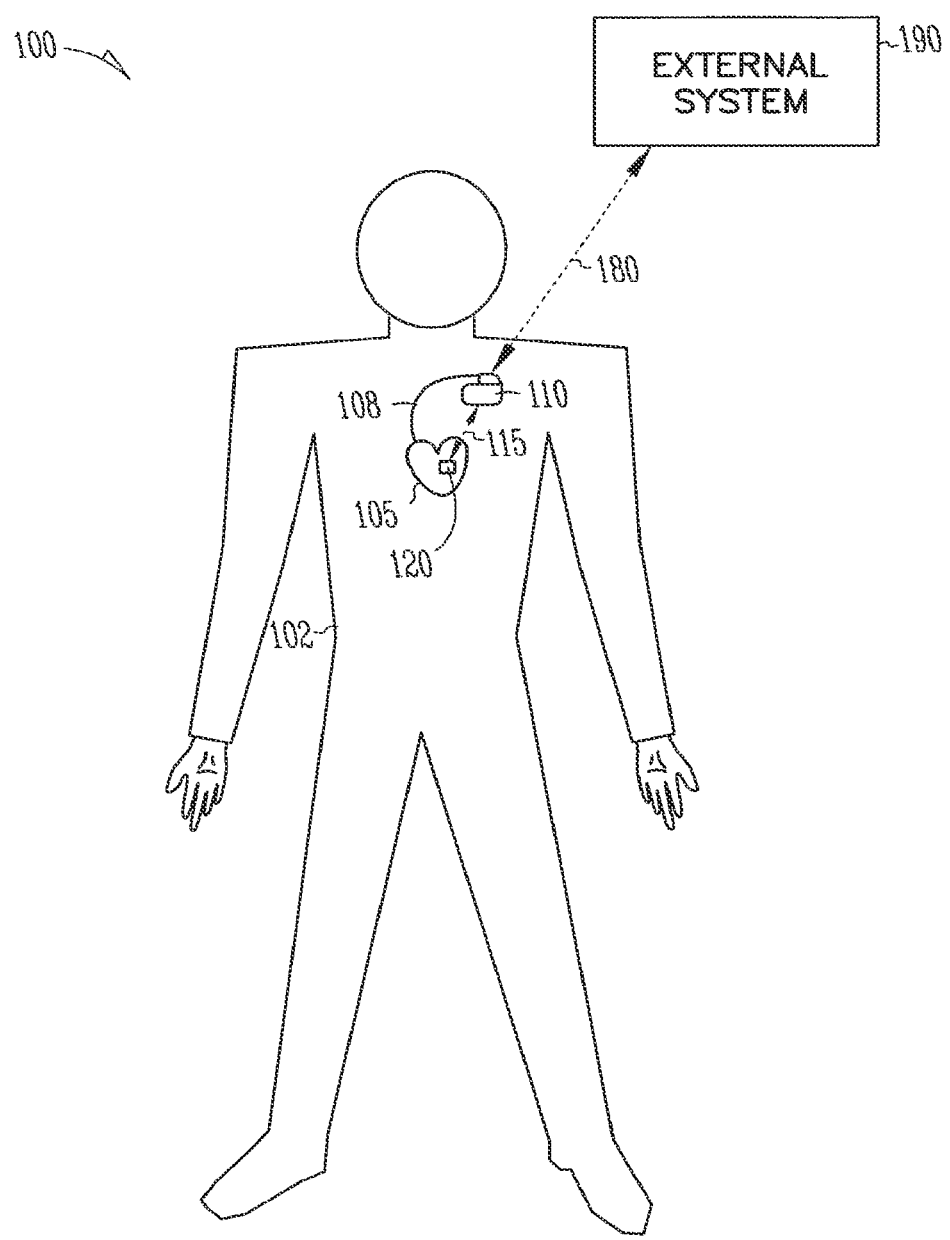
FIG. 1 is an illustration of an embodiment of portions of a CRM system and portions of an environment in which it is used.

FIG. 1 is a block diagram illustrating an embodiment of a CRM system 100, and portions of an environment in which system 100 is used. System 100 includes an implantable medical device 110, a lead system 108, another implantable medical device 120, and an external system 190. An acoustic couple 115 provides for communication between implantable medical device 110 and implantable medical device 120. A wireless telemetry link 180 provides for communication between implantable medical device 110 and external system 190.

After implantation, implantable medical device 110 operates within a body 102 of a patient to sense activities of a heart 105 and deliver one or more therapies to heart 105 through lead system 108. In one embodiment, as illustrated in FIG. 1, implantable medical device 110 is an implantable CRM device that delivers one or more therapies including, but are not limited to, a pacing therapy, a cardioversion/defibrillation therapy, a cardiac resynchronization therapy (CRT), a remodeling control therapy (RCT), a drug therapy, and a biological therapy such as a cell therapy and a gene therapy. Implantable medical device 120 also operates within body 102 to perform one or more sensing and/or therapeutic functions. In one embodiment, implantable medical device 120 supports or supplements one or more functions of implantable medical device 110. Acoustic couple 115 allows implantable medical device 110 and implantable medical device 120 to communicate with each other when a wired connection between the two implantable medical devices is difficult to implement because of, for example, anatomical structure of body 102.

Lead system 108 provides one or more electrical connections between implantable medical device 110 and heart 105. In one embodiment, lead system 108 includes one or more leads each including one or more electrodes configured for endocardial and/or epicardial placement. Pacing and/or cardioversion/defibrillation are delivered to heart 105 through such leads and electrodes. In one embodiment, one or more leads of lead system 108 also include therapy delivery ports configured for endocardial, epicardial, and/or intravascular placement. Substances such as chemical or biological agents are delivered to heart 105 through such leads and therapy delivery ports.

In one embodiment, implantable medical device 120 includes an implantable sensing module. In one specific embodiment, the implantable sensing module is a pressure sensing module implanted in the left ventricle (LV) to sense an LV pressure that is used by implantable medical device 110 as a signal controlling its therapy delivery function. The use of such an implantable sensing module allows LV pressure sensing while avoiding the difficulty associated with accessing the LV using an implantable pressure catheter connected to implantable medical device 110. In other specific embodiments, the implantable sensing module is used to sense a pulmonary pressure or an aortic pressure while avoiding the use of an implantable pressure catheter that has to pass two cardiac valves to connect to implantable medical device 110. Acoustic couple 115 provides for communications between implantable medical device 110 and implantable medical device 120. In one embodiment, where implantable medical device 120 is a pressure sensing module employed for sensing an intracardiac or intravascular pressure, implantable medical device 110 sends a command via acoustic couple 115 to activate implantable medical device 120 when the pressure sensing is needed. In response, implantable medical device 120 is activated and sends data representative of the sensed pressure to implantable medical device 110 via acoustic couple 115.

Acoustic couple 115 is a data communication link formed between two acoustic couplers. When being used for intra-body communications, acoustic communication is substantially more energy-efficient when compared to telemetry communication based on inductive couple (magnetic field) or radio-frequency electromagnetic waves. Implantable medical device 110 and implantable medical device 120 each include an acoustic coupler, which includes an acoustic transducer. The acoustic transducer converts electrical energy to acoustic energy for transmitting a signal and converts acoustic energy to electrical energy for receiving a signal. The acoustic signals usable for intra-body communication purposes include audible and ultrasonic signals. The carrier frequency for the acoustic signals can be up to 5 MHz. In one embodiment, the carrier frequency range is generally within an ultrasonic range. The lower bound of the carrier frequency range is chosen based on considerations of patient's audio perception of the acoustic signal and the design constraints of the acoustic transducer, and the upper bound of the frequency range is chosen based on considerations of tissue absorption of the acoustic energy and the directionality of the acoustic transducer in transmitting and receiving audio signals. The carrier frequency is chosen to avoid using an acoustic signal audible to the patient. Structural constraints, such as size and material, that generally apply to implantable medical device 110 also affect the selection of the carrier frequency. For example, size of the transducer, stiffness of the support structure to which the transducer is attached, and whether the transducer is to operate in resonance are among the factors to be considered in selecting the carrier frequency. Such factors are dependent on the overall size, material, and structure of implantable medical device 110. In one specific embodiment, the lower bound of the carrier frequency is about 30 kHz. The tissue absorption of acoustic energy generally increases with the frequency of the acoustic signal, making acoustic communication less energy-efficient at higher frequencies. The degree of directionality also generally increases with the frequency of the acoustic signal, making an acoustic coupler more directional (i.e., covering a smaller space) at higher frequencies. In one embodiment, the upper bound of the frequency range is about 60 kHz, where the tissue absorption is not considered significant and an approximately omnidirectional acoustic coupler can be implemented. An omnidirectional acoustic coupler is desirable because the acoustic communication is not affected by the relative positions of the implantable medical device 110 and implantable medical device 120, which change as the patient makes a movement.

External system 190 communicates with implantable medical device 110 via telemetry link 180. External system 190 allows a physician or other caregiver to communicate with implantable medical device 110. In one embodiment, external system 190 includes an external programmer. In another embodiment, external system 190 includes a patient management system including an external device communicating with implantable medical device 110 via telemetry link 180, a network coupled to the external device, and a remote device coupled to the network. Such a patient management system allows a physician or other caregiver to communicate with implantable medical device 110 through the remote device in a distant location. In one embodiment, the physician or other caregiver also communicates with implantable medical device 120.

Telemetry link 180 provides for data transmissions between implantable medical device 110 and external system 190. In one embodiment, telemetry link 180 also provides for data transmissions between implantable medical device 120 and external system 190. In another embodiment, implantable medical device 120 and external system 190 communicate via acoustic couple 115 and telemetry link 180, using implantable medical device 110 as a repeater. In one embodiment, telemetry link 180 is an inductive telemetry link. In an alternative embodiment, telemetry link 180 is a far-field radio-frequency telemetry link. In another alternative embodiment, telemetry link 180 is another acoustic couple. An acoustic coupler device of external system 190 includes an acoustic transducer that is to be attached to the skin of the patient such that intra-body acoustic communication can be performed using body 102 as the medium. Data transmission provided by telemetry link 180 may include, for example, transmitting real-time physiological data acquired by implantable medical devices 110 and/or 120, extracting physiological data acquired by and stored in implantable medical devices 110 and/or 120, extracting therapy history data stored in implantable medical devices 110 and/or 120, and extracting data indicating an operational status of implantable medical devices 110 and/or 120 (e.g., battery status and lead impedance). Telemetry link 180 also provides for data transmission from external system 190 to implantable medical devices 110 and/or 120. This may include, for example, programming implantable medical devices 110 and/or 120 to acquire physiological data, programming implantable medical devices 110 and/or 120 to perform at least one self-diagnostic test (such as for a battery status and lead impedance status), and programming implantable medical devices 110 and/or 120 to deliver at least one therapy. Examples of signals represented by the physiological data include, but are not limited to, electrograms, heart sounds or signals indicative of heart sounds, activity level signals, pressure signals, impedance signals, and respiratory signals. In one embodiment, the physiological data also include parameters measured from one or more of these signals. In one embodiment, external system 190 or the physician or other caregiver determines and/or adjusts a therapy based on these signals and/or physiological data.

Figure 2:
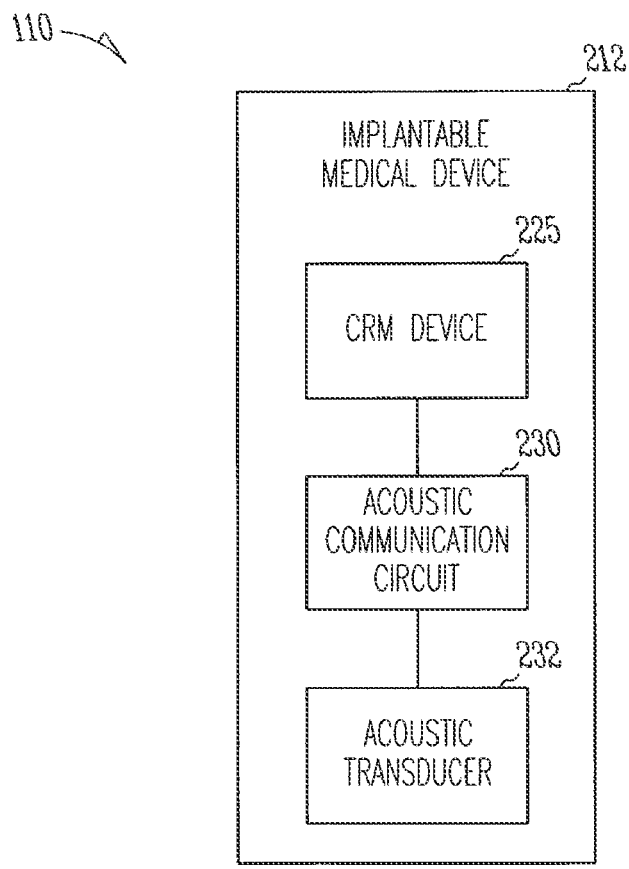
FIG. 2 is block diagram illustrating one embodiment of a circuit of an implantable medical device with an acoustic transducer as an acoustic coupler for the acoustic communication.

FIG. 2 is block diagram illustrating one embodiment of a circuit of implantable medical device 110. Implantable medical device 110 includes a CRM device 225, an acoustic communication circuit 230, and an acoustic transducer 232. CRM device 225 includes one or more of a sensing circuit to sense one or more physiologic signals and a therapy delivery circuit. CRM device 225 includes, but is not limited to, one or more of a monitoring device sensing one or more physiologic signals, a pacing device, a cardioversion/defibrillation device, a CRT device, an RCT device, a drug delivery device, a cell therapy device, a gene therapy device, and a therapy delivery controller device. Acoustic communication circuit 230 is connected to acoustic transducer 232, which is used as the acoustic coupler for the acoustic communication. CRM device 225 and acoustic circuit 230, or portions of each, are encapsulated by an implantable housing 212 to form implantable medical device 110.

Acoustic transducer 232 includes one or more piezoelectric transducers. The piezoelectric transducer is made of a piezoelectric material such as polyvinylidene fluoride (PVDF) or piezoelectric ceramic. In one embodiment, acoustic transducer 232 includes a single piezoelectric transducer. In another embodiment, acoustic transducer 232 is an acoustic transducer array including a plurality of acoustic transducers each being a piezoelectric transducer. In one specific embodiment, acoustic transducer 232 includes a microelectromechanical acoustic transducer array (MEMS-UTA). In one embodiment, a piezoelectric transducer functions as an approximately omni-directional acoustic coupler for the acoustic communication. In another embodiment, a piezoelectric transducer functions as a directional acoustic coupler having a directionality of greater than 180 degrees to cover more than a hemispherical space. In another embodiment, a piezoelectric transducer functions as a directional acoustic coupler having a directionality of less than 180 degrees. In one embodiment, an acoustic transducer array including a plurality of piezoelectric transducers each having a limited directionality. A transducer interface circuit is connected to the acoustic transducer array to make it an electronically steerable acoustic coupler.

In general, acoustic communication circuit 230 and acoustic transducer 232, including their various embodiments, provide acoustic communication to an implantable medical device used in CRM or other applications. In non-CRM embodiments, CRM device 225 is replaced by a non-CRM device that includes at least one of a monitoring device to sense one or more physiologic signals and a therapy delivery device. In one embodiment, an implantable medical device includes a monitoring device coupled to acoustic communication circuit 230 and acoustic transducer 232. The monitoring device includes one or more sensors to sense one or more physiologic signals. In another embodiment, an implantable medical device includes an electrical stimulation device coupled to acoustic communication circuit 230 and acoustic transducer 232. Examples of the electrical stimulation device include a neural stimulation device and a neuromuscular stimulation device. In another embodiment, an implantable medical device includes a drug delivery device coupled to acoustic communication circuit 230 and acoustic transducer 232. The drug delivery device delivers one or more of chemical, biochemical, and biological agents intended for use in the diagnosis, cure, mitigation, treatment, or prevention of one or more diseases.

Figures 3A, 3B:
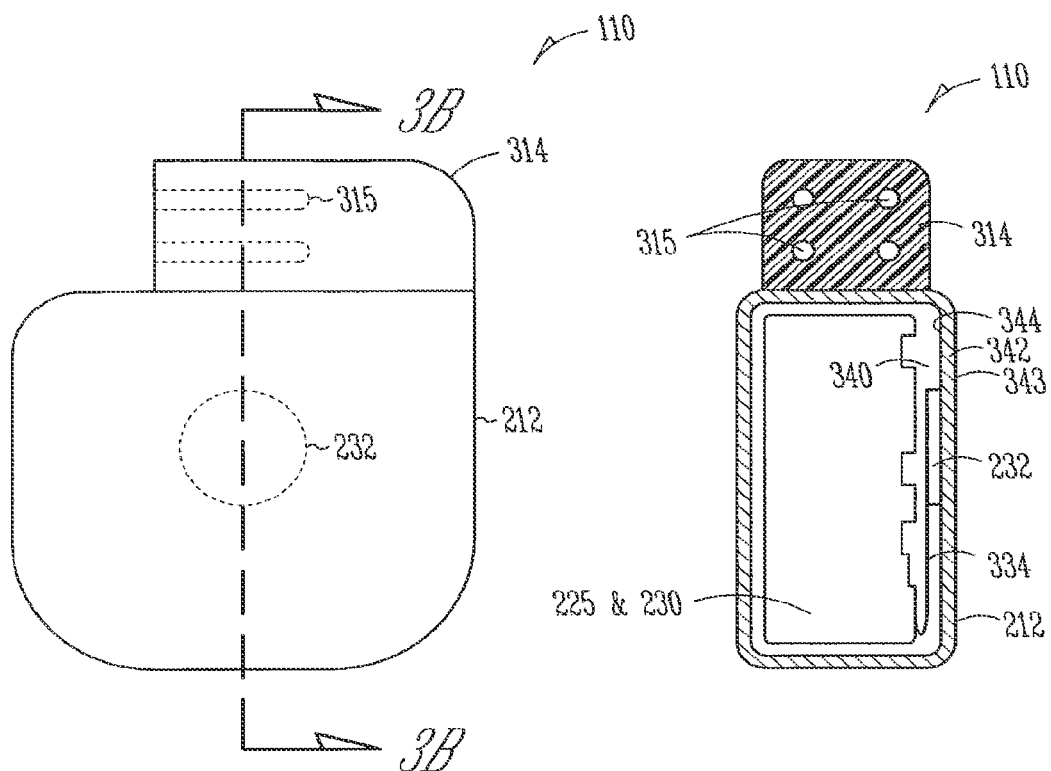
FIG. 3A is a side view.
FIG. 3B is a corresponding cross-sectional view, illustrating one embodiment of the implantable medical device with the acoustic transducer.

FIG. 3A is a side view, and FIG. 3B is a corresponding cross-sectional view, illustrating one embodiment of implantable medical device 110 with acoustic transducer 232 as the acoustic coupler for the acoustic communication. Implantable medical device 110 includes implantable housing 212, which is hermetically sealed and contains electronic circuitry and other structural components. Implantable housing 212 includes a wall 342 forming a chamber 340 that contains CRM device 225 and acoustic communication circuit 230 or portions of each. Wall 342 has an exterior surface 343 and an interior surface 344. Interior surface 344 is the surface facing chamber 340 (i.e., on the side of chamber 340). Acoustic transducer 232 is fastened to wall 343 and connected to acoustic communication circuit 230 through an interconnection cable 334. The thickness of a piezoelectric transducer is on the order of 0.1 mm and is typically less than 0.5 mm, making acoustic transducer 232 physically suitable for inclusion in implantable medical device 110 and attachment to wall 343. In one embodiment, interconnection cable 334 is a strip cable. In another embodiment, interconnection cable 334 is a spring cable. A header 314 is attached to implantable housing 212. Header 314 includes connectors 315 that provide for an interface between implantable medical device 110 and lead system 108. The size and shape of each component, as well as the number of connector 315 and the number of interconnection cable 334, as shown in FIGS. 3A and 3B are for illustrative purpose only and not for any restrictive purpose.

In one embodiment, implantable housing 212 is a can made of a biocompatible metallic material such as titanium. Acoustic transducer 232 is fastened to wall 342 using any method that provides a permanent attachment of the transducer to the wall. In one embodiment, acoustic transducer 232 is glued to wall 342 using a medical grade adhesive such as medical grade epoxy. In another embodiment, acoustic transducer 232 is spot-welded to wall 342. In another embodiment, acoustic transducer 232 is soldered to wall 342. In another embodiment, acoustic transducer 232 is braced to wall 342. Specific examples of acoustic transducer 232 fastened to a portion of implantable medical device 110 are discussed below with reference to FIGS. 4-12.

Figure 4:
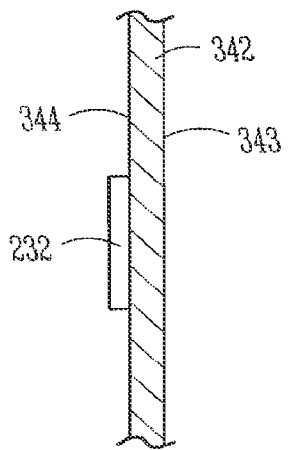
FIG. 4 is a cross-sectional view illustrating one embodiment of the acoustic transducer fastened to a portion of the implantable medical device.

FIG. 4 is a cross-sectional view illustrating one embodiment of acoustic transducer 232 fastened to a portion of implantable medical device 110. In this embodiment, acoustic transducer 232 is fastened to interior surface 344 of wall 342. Thus, acoustic transducer 232 is within chamber 340, inside the hermetically sealed implantable housing 212.

Figure 5:
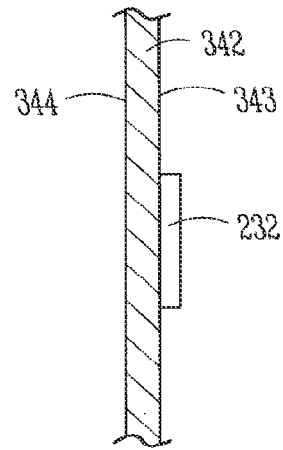
FIG. 5 is a cross-sectional view illustrating another embodiment of the acoustic transducer fastened to a portion of the implantable medical device.

FIG. 5 is a cross-sectional view illustrating another embodiment of acoustic transducer 232 fastened to a portion of implantable medical device 110. In this embodiment, acoustic transducer 232 is fastened to exterior surface 343 of wall 342. Acoustic transducer 232 is made biocompatible. In one embodiment, acoustic transducer 232 includes one or more transducers made of a biocompatible piezoelectric material. In another embodiment, acoustic transducer 232 includes one or more transducers coated with a biocompatible material.

Figure 6:
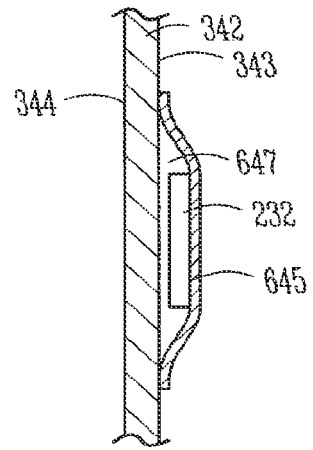
FIG. 6 is a cross-sectional view illustrating another embodiment of the acoustic transducer fastened to a portion of the implantable medical device.

FIG. 6 is a cross-sectional view illustrating another embodiment of acoustic transducer 232 fastened to a portion of implantable medical device 110. In this embodiment, a diaphragm 645 is connected to exterior surface 343 of wall 342 to form an isolated cavity 647 between diaphragm 645 and exterior surface 343. Acoustic transducer 232 is fastened to diaphragm 645 and is within cavity 647. Diaphragm 645 is sufficiently thin to be acoustically transparent, i.e., to have minimal acoustic absorption, and protects acoustic transducer 232, such as from effects of tissue growth. In one embodiment, diaphragm 645 and implantable housing 212 are made of the same type biocompatible metal, such as titanium. In another embodiment, diaphragm 645 and implantable housing 212 are made of different type biocompatible metals. In one embodiment, diaphragm 645 is welded to exterior surface 343. Acoustic transducer 232 is connected to acoustic communication circuit 230 via one or more hermetically sealed feedthroughs across wall 342. Damage to diaphragm 645 does not destroy the hermetical sealing of implantable housing 212.

In one embodiment, diaphragm 645 is configured to have a resonant frequency approximately equal to the carrier frequency of the acoustic signal. This increases the efficiency of the acoustic transmission. Resonance occurs at a primary frequency and its harmonic frequencies, thus providing a number of frequencies that can be used as the carrier frequency of the acoustic communication when maximum efficiency is sought. In one embodiment, diaphragm 645 is substantially thinner than wall 342 to provide a resonance frequency in the carrier frequency range for the acoustic communication, e.g., about 30 kHz-60 kHz. When acoustic transducer 232 is fastened to a thicker diaphragm 645 or wall 342, the efficiency for the acoustic communication is lower.

Figure 7:
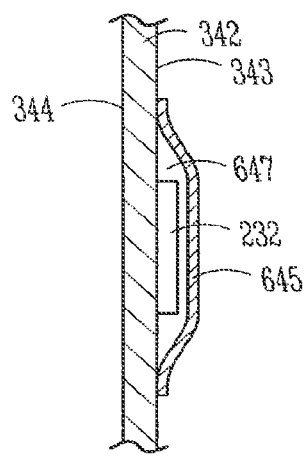
FIG. 7 is a cross-sectional view illustrating another embodiment of the acoustic transducer fastened to a portion of the implantable medical device.

FIG. 7 is a cross-sectional view illustrating another embodiment of acoustic transducer 232 fastened to a portion of implantable medical device 110. In this embodiment, diaphragm 645 is connected to exterior surface 343 of wall 342 to form isolated cavity 647 between diaphragm 645 and exterior surface 343. Acoustic transducer 232 is fastened to exterior surface 343 of wall 342 and is within cavity 647. This embodiment differs from the embodiment illustrated in FIG. 6 in that acoustic transducer 232 is fastened to exterior surface 343 of wall 342 instead of diaphragm 645. Hermetically sealed cavity 647 is filled with fluid, such as gel. The fluid functions as medium for the acoustic communication between diaphragm 645 and acoustic transducer 232.

Figure 8:
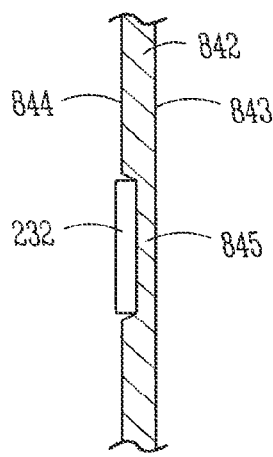
FIG. 8 is a cross-sectional view illustrating another embodiment of the acoustic transducer fastened to a portion of the implantable medical device.

FIG. 8 is a cross-sectional view illustrating another embodiment of acoustic transducer 232 fastened to a portion of implantable medical device 110. In this embodiment, a wall 842 represents an alternative embodiment of wall 342 of implantable housing 212. Wall 842 includes an exterior surface 843 corresponding to exterior surface 343 and an interior surface 844 corresponding to interior surface 344. Wall 842 includes a thinned portion forming a diaphragm 845. Acoustic transducer 232 is fastened to diaphragm 845 on the side of interior surface 844, within the chamber formed by wall 843. By resonance, diaphragm 845 provides a higher efficiency for the acoustic communication when compared to other portions of wall 842 (or wall 342).

Figure 9:
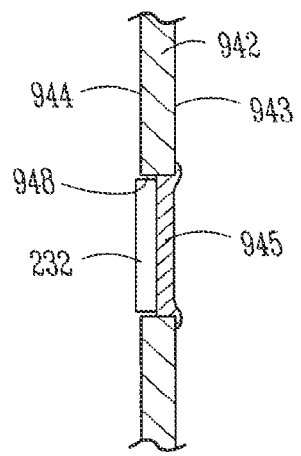
FIG. 9 is a cross-sectional view illustrating another embodiment of the acoustic transducer fastened to a portion of the implantable medical device.

FIG. 9 is a cross-sectional view illustrating another embodiment of acoustic transducer 232 fastened to a portion of implantable medical device 110. In this embodiment, a wall 942 represents an alternative embodiment of wall 342 of implantable housing 212. Wall 942 includes an exterior surface 943 corresponding to exterior surface 343 and an interior surface 944 corresponding to interior surface 344. Wall 942 includes a hole 948. A diaphragm 945 is connected to wall 942 over the hole. Acoustic 232 is fastened to diaphragm 945 on the side of interior surface 944, within the chamber formed with wall 942. In one embodiment, diaphragm 945 is welded to wall 942. The connection between diaphragm 945 and wall 942 is hermetically sealed. By resonance, diaphragm 945 provides a higher efficiency for the acoustic communication when compared to other portions of wall 942 (or wall 342).

Figure 10:
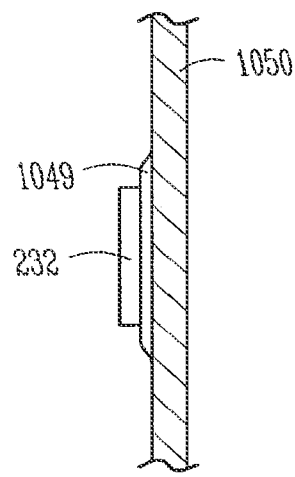
FIG. 10 is a cross-sectional view illustrating another embodiment of the acoustic transducer fastened to a portion of the implantable medical device.

FIG. 10 is a cross-sectional view illustrating another embodiment of acoustic transducer 232 fastened to a portion of implantable medical device 110. In this embodiment, a wall 1050 represents a sheet structure being a portion of implantable medical device 110, such as a wall (342, 842, or 942) or a diaphragm (645, 845, or 945). A coating 1049 with a predetermined stiffness is applied to a portion of wall 1050, on either of its surfaces, and acoustic transducer 232 is fastened to wall 1050 over coating 1049. Coating 1049 provides a desirable resonant frequency that is difficult to provide with wall 1050 alone. The resonant frequency depends on the thickness of wall 1050, the thickness of coating 1049, and the properties of each of wall 1050 and coating 1049 including stiffness.

Figure 11:
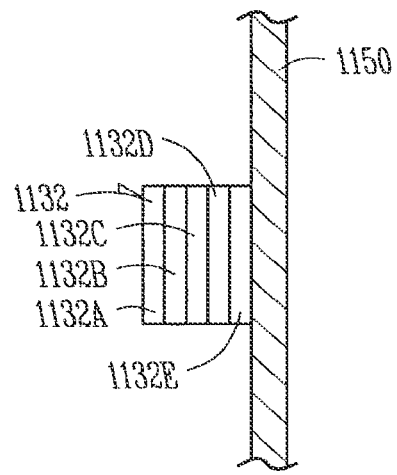
FIG. 11 is a cross-sectional view illustrating one embodiment of multiple acoustic transducers fastened to a portion of the implantable medical device.

FIG. 11 is a cross-sectional view illustrating one embodiment of an acoustic transducer 1132 to a portion of implantable medical device 110. Acoustic transducer 1132 represents one specific embodiment of acoustic transducer 232 and includes stacked acoustic transducers 1132A-E each being a piezoelectric transducer. The number of the transducers included in acoustic transducer 1132 as shown in FIG. 11 is for illustrative purpose only and not for any restrictive purpose. In one embodiment, the total height of the stacked acoustic transducers 1132A-E is limited to about 1.0 mm or any other height suitable for inclusion in implantable medical device 110. A wall 1150 represents a sheet structure being a portion of implantable medical device 110, such as a wall (342, 842, or 942) or a diaphragm (645, 845, or 945). Stacked acoustic transducers 1132A-E are fastened to either surface (side) of wall 1150. In one embodiment, acoustic transducers 1132A-E are connected in series and then connected to acoustic communication circuit 230. In another embodiment, acoustic transducers 1132A-E are connected in parallel and then connected to acoustic communication circuit 230. In another embodiment, a programmable interconnection network provides the interconnections among acoustic transducers 1132A-E. Such interconnections are made in accordance with impedance matching requirements, signal amplitude requirements, and signal-to-noise ratio requirements, which are dependent on the physical dimensions of each acoustic transducer. In one embodiment, acoustic transducers 1132A-E are connected in series when acoustic communication circuit 230 receives an incoming acoustic signal and in parallel when acoustic communication circuit 230 transmits an outgoing acoustic signal.

Figure 12A:
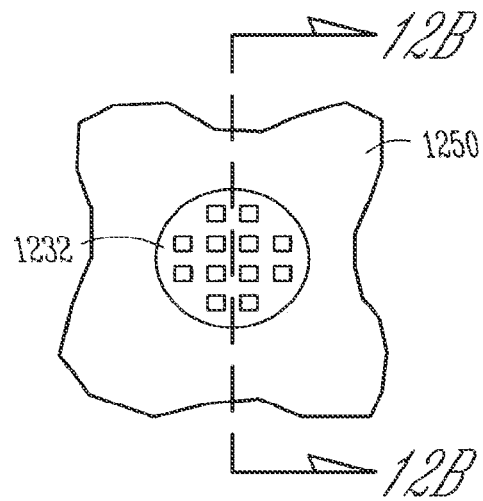
FIG. 12A is a side view.
Figure 12B:
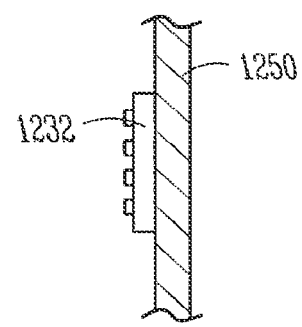
FIG. 12B is a corresponding cross-sectional view, illustrating one embodiment of an acoustic transducer array fastened to a portion of the implantable medical device.

FIG. 12A is a side view, and FIG. 12B is a corresponding cross-sectional view, illustrating one embodiment of an acoustic transducer 1232 fastened to a portion of implantable medical device 110. Acoustic transducer 1232 represents one specific embodiment of acoustic transducer 232 and includes an array of acoustic transducers each being a piezoelectric transducer. In one embodiment, acoustic transducer 1232 is an MEMS-UTA. The number and layout of the transducers in acoustic transducer 1232 as shown in FIG. 12 are for illustrative purpose only and not for any restrictive purpose. A wall 1250 represents a sheet structure being a portion of implantable medical device 110, such as a wall (342, 842, or 942) or a diaphragm (645, 845, or 945). Acoustic transducer 1232 is fastened to either surface (side) of wall 1250. In one embodiment, a transducer interface circuit provides programmable tuning for each transducer of the array of acoustic transducers. In one embodiment, the array of acoustic transducers form an acoustic coupler having a directionality and effective orientation each electronically controllable through the transducer interface circuit. In one specific embodiment, the transducer interface circuit drives each transducer of the array of acoustic transducers with a programmable phase delay. The directionality and effective orientation of the acoustic coupler is controlled by programming the phase delays.

Figure 13:
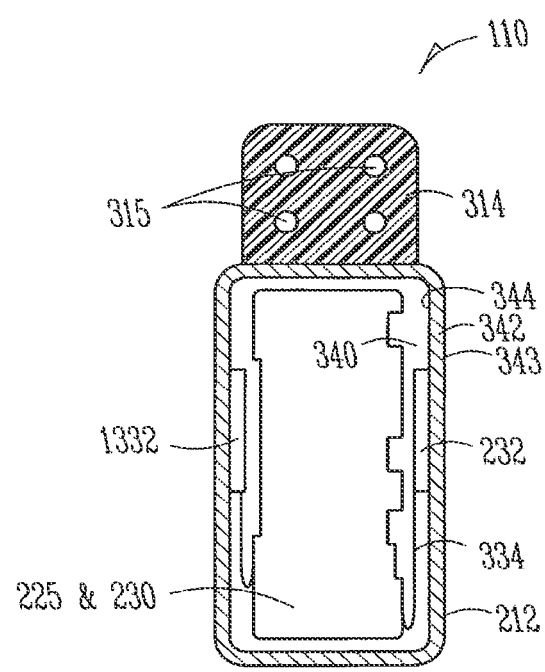
FIG. 13 is a cross-sectional view illustrating one embodiment of an implantable medical device with two acoustic transducers for acoustic communication.

FIG. 13 is a cross-sectional view illustrating one embodiment of implantable medical device 110 with two acoustic transducers for the acoustic communication. In this embodiment, implantable medical device 110 includes acoustic transducer 232 and a second acoustic transducer 1332. Acoustic transducers 232 and 1332 each have a directionality of approximately 180 degrees or a directionality of greater than 180 degrees but substantially smaller than 360 degrees. Being fastened to opposite sides of implantable housing 212 and facing opposite directions, acoustic transducers 232 and 1332 form an acoustic coupler system that is substantially omni-directional.

Figure 14:
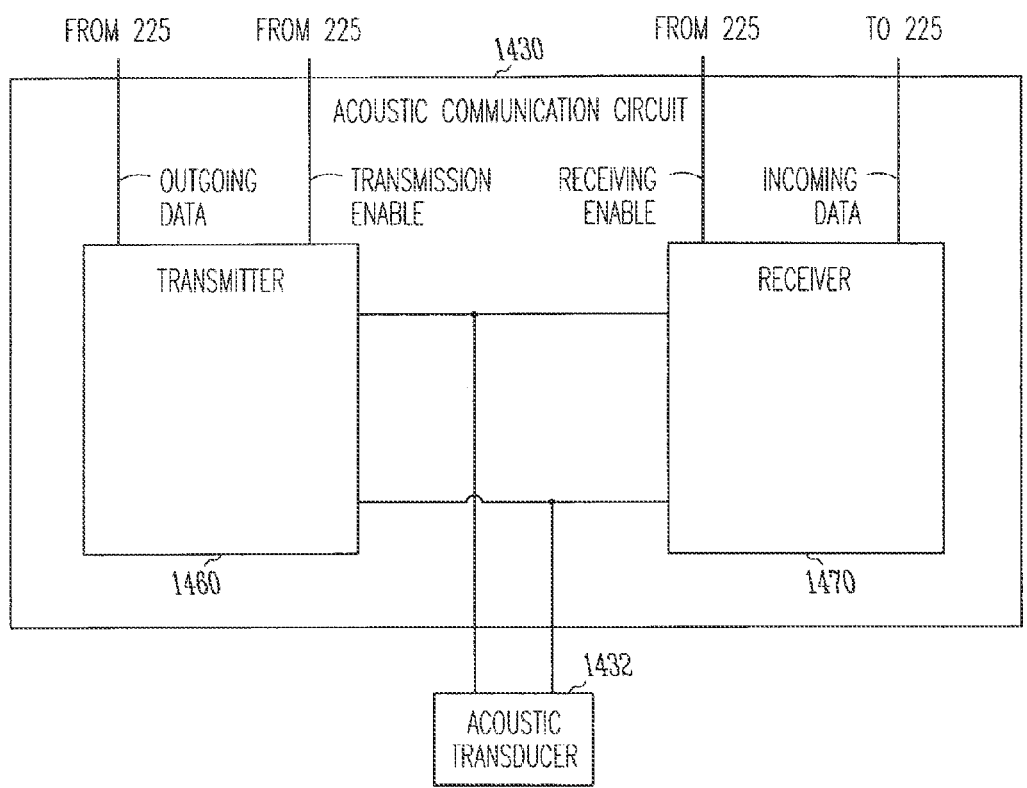
FIG. 14 is a block diagram illustrating one embodiment of an acoustic communication circuit of the implantable medical device.

FIG. 14 is a block diagram illustrating one embodiment of an acoustic communication circuit 1430, which represents one embodiment of acoustic communication circuit 230. A control circuit in CRM device 225 controls the operation of acoustic communication circuit 1430, including enablement of one of receiving data and transmitting data. An acoustic transducer 1432 represents one specific embodiment of acoustic transducer 232, or generally, an acoustic coupler including one or more acoustic transducers. A transmitter 1460 and a receiver 1470 are connected to acoustic transducer 1432. After being enabled by a transmission enable signal generated by the control circuit in CRM device 225, transmitter 1460 produces an outgoing acoustic signal modulated by outgoing data from CRM device 225. After being enabled by a receiving enable signal generated by the control circuit in CRM device 225, receiver 1470 receives an incoming acoustic signal modulated by incoming data from another device such as implantable medical device 120. Transmitter 1460 and receiver 1470 are enabled one at a time such that acoustic transducer 1432 are used for both transmitting and receiving acoustic signals.

In one embodiment, the outgoing data and the incoming data are both binary data. The outgoing acoustic signal and the incoming acoustic signal each include a carrier signal modulated by data using one of amplitude-shift keying (ASK), frequency-shift keying (FSK), and phase-shift keying (PSK). In one embodiment, to keep acoustic communication circuit 1430 simple, ASK is chosen as the modulation scheme. In one specific embodiment, on-off keying (OOK), or ASK with near 100% modulation index, is chosen as the modulation scheme.

Figure 15:
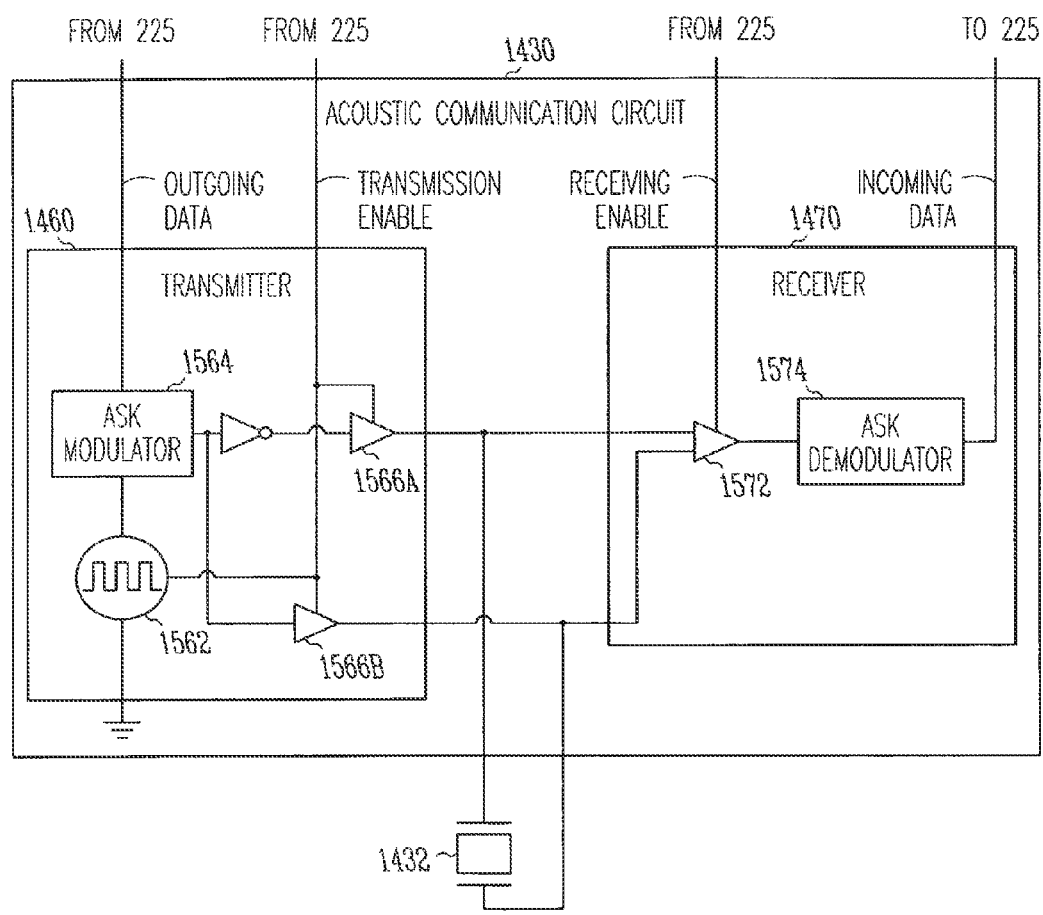
FIG. 15 is a schematic/block diagram illustrating details of the acoustic communication circuit of FIG. 14.

FIG. 15 is a schematic/block diagram illustrating additional details of transmitter 1460 and receiver 1470 of acoustic communication circuit 1430. Transmitter 1460 includes a carrier generator 1562, an ASK modulator 1564, and buffers 1566A and 1566B. Carrier generator 1562 generates the carrier signal for the acoustic communication. In one embodiment, the carrier signal is a square wave. In one embodiment, the frequency of the carrier signal is within a range of about 30 kHz-60 kHz. ASK modulator 1564 modulates the carrier signal received from carrier generator 1562 with the outgoing data received from CRM device 225. The resultant outgoing acoustic signal is applied to acoustic transducer 1432 through buffers 1566A and 1566B when these buffers are enabled for passing signals by the transmission enable signal. Receiver 1470 includes a buffer or amplifier 1572 and an ASK demodulator 1574. ASK demodulator 1574 receives an incoming signal from acoustic transducer 1432 through buffer or amplifier 1572 when the buffer or amplifier is enabled for passing signal by the receiving enable signal. ASK demodulator 1574 demodulates the incoming signal to recover the incoming data. The incoming data are then sent to CRM device 225.

Figure 16:
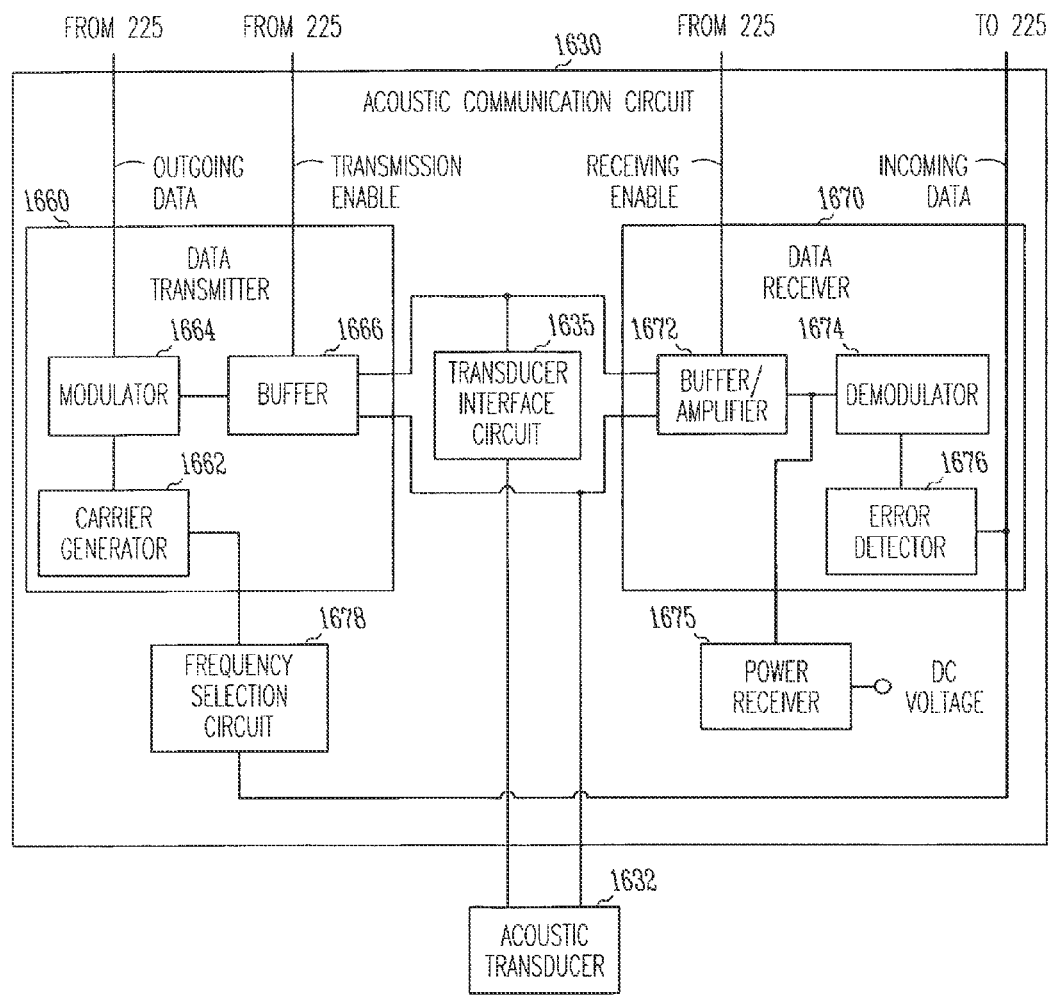
FIG. 16 is a schematic/block diagram illustrating another embodiment of the acoustic communication circuit.

FIG. 16 is a schematic/block diagram illustrating an acoustic communication circuit 1630, which represents another embodiment of acoustic communication circuit 230. Acoustic communication circuit 1630 is connected to an acoustic transducer 1632 and includes a transducer interface circuit 1635, a data transmitter 1660, a data receiver 1670, a power receiver 1675, and a frequency selection circuit 1678. In various embodiments, acoustic communication circuit 230 includes components including, but not being limited to, some or all components of acoustic communication circuit 1630 as illustrated in FIG. 16.

Acoustic transducer 1632 represents one specific embodiment of acoustic transducer 232 or generally, an acoustic coupler including one or more acoustic transducers. In one embodiment, transducer interface circuit 1635 includes a tuning circuit. The tuning circuit provides a desirable quality factor (Q) for the acoustic coupler. In another embodiment, transducer interface circuit 1635 includes impedance matching circuitry for impedance matching between acoustic transducer 1635 and acoustic communication circuit 1630. In another embodiment, in which acoustic transducer 1632 includes stacked multiple acoustic transducers, such as stacked multiple acoustic transducers 1132A-E, transducer interface circuit 1635 includes the programmable interconnections network to control an impedance of acoustic transducer 1632. In another embodiment, in which acoustic transducer 1632 includes an acoustic transducer array such as acoustic transducer 1232, transducer interface circuit 1635 includes a steering circuit to electronically control the directionality and effective orientation of acoustic transducer 1632 as the acoustic coupler. In one specific embodiment, the steering circuit controls the directionality and effective orientation of acoustic transducer 1632 by applying an individually programmed phase delay to each transducer of the acoustic transducer array.

Data transmitter 1660 includes a carrier generator 1662, a modulator 1664, and a buffer 1666. Carrier generator 1662 generates the carrier signal for the acoustic communication. In one embodiment, the carrier signal is a square wave. In one embodiment, the frequency of the carrier signal is within a range of about 30 kHz-60 kHz. Modulator 1664 modulates the carrier signal received from carrier generator 1662 with the outgoing data received from CRM device 225. The resultant outgoing acoustic signal is applied to acoustic transducer 1632 through buffer 1666 when the buffer is enabled for passing signals by the transmission enable signal received from CRM device 225. Data receiver 1670 includes a buffer or amplifier 1672, a demodulator 1674, and an error detector 1676. Demodulator 1674 receives an incoming signal from acoustic transducer 1632 through buffer or amplifier 1672 when the buffer is enabled for passing signal by the receiving enable signal received from CRM device 225. Demodulator 1674 demodulates the incoming signal to receive the incoming data. Error detector 1676 detects errors from the incoming data to determine an error rate. The incoming data are sent to CRM device 225 if the error rate is below a predetermined threshold rate.

Power receiver 1675 receives the acoustic signal from acoustic transducer 1632 through buffer or amplifier 1672 when the buffer is enabled and recovers direct current (dc) energy from the incoming acoustic signal. An external device including an acoustic transducer is used to transmit energy to implantable medical device 110 through acoustic transducer 1632. In one embodiment, power receiver 1675 includes a rectifier circuit and a low-pass filter to convert the acoustic signal to a dc voltage, which is then used to recharge a rechargeable battery being a power supply of implantable medical device 110. Though it may take several days to fully recharge a substantially depleted rechargeable battery, this method can be applied to partially recharge a rechargeable battery, for example, whenever the external device is coupled to implantable medical device 110.

Figure 17:
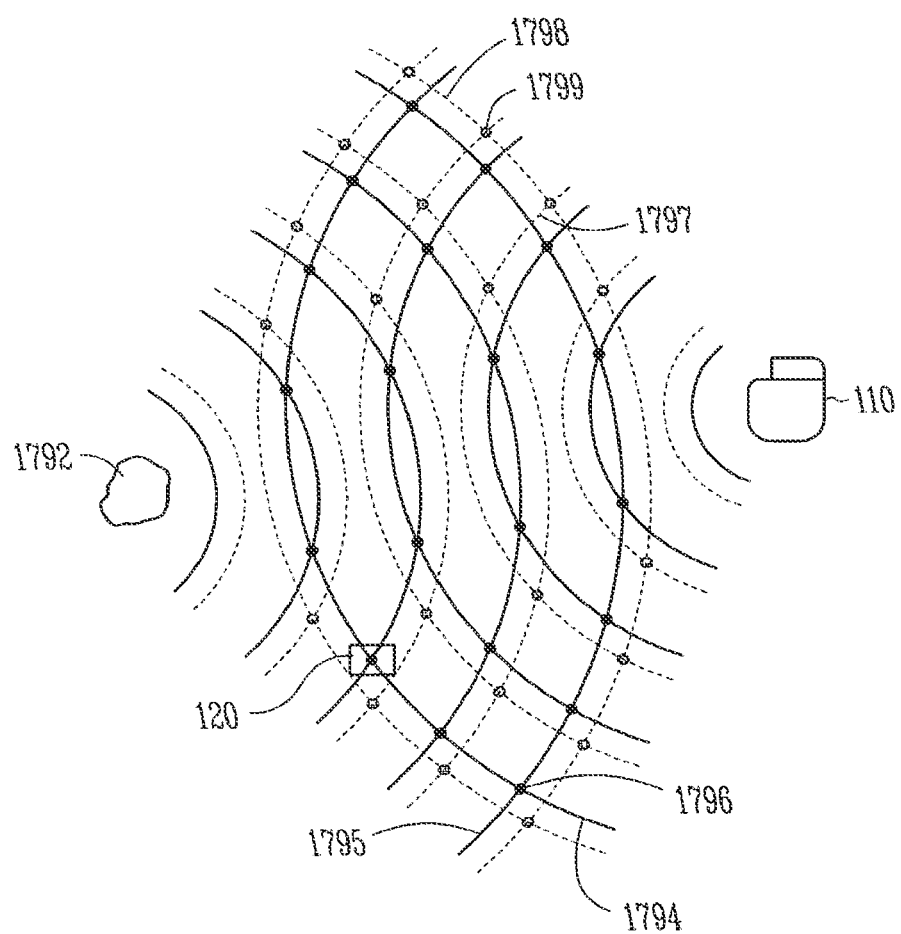
FIG. 17 is a diagram illustrating a need for frequency diversity.

In one embodiment, acoustic couple 115 employs frequency diversity for a reliable acoustic communication between implantable medical device 110 and implantable medical device 120. Two or more substantially different frequencies are used as carrier frequencies of the acoustic signal. FIG. 17 is a diagram illustrating the need for frequency diversity. An acoustic signal is transmitted from implantable medical device 110 to be received by implantable medical device 120. The acoustic wave propagated from implantable medical device 110 is reflected at boundaries of different anatomical structures within body 102. As illustrated in FIG. 17, the acoustic wave is reflected at a reflector 1792, which is an anatomic structure such as a bone. Solid lines 1794 represent equipotential surfaces of the incident acoustic wave propagated from the acoustic transducer of implantable medical device 110. Solid lines 1795 represent equipotential surfaces of the reflected acoustic wave due to reflector 1792. The positions of solid lines 1794 and solid line 1795 are a function of the carrier frequency of the acoustic signal. One effect of the reflection of the acoustic wave caused by reflector 1792 is "nulls" distributed in body 102. The nulls are illustrated as solid dots 1796. Each null represents a point where the incident acoustic wave and the reflected acoustic wave cancel out. If the acoustic transducer of implantable medical device 120 happens to coincide with one of the nulls, it does not receive the acoustic signal. Due to the body anatomy and movements of the patient, numerous reflectors exist in body 102 and their location relative to implantable medical devices 110 and 120 change from time to time. The relative locations of implantable medical devices 110 and 120 also change for the same reason. It is therefore infeasible to avoid the nulls by choosing implantation sites for implantable medical devices 110 and 120.

One approach to ensure substantially uninterrupted reception of the acoustic signal is frequency diversity. If the acoustic signal at a first carrier frequency is not receivable due to a null, a substantially different second carrier frequency is used. In FIG. 17, solid lines 1794 represent equipotential lines of the incident wave, and solid lines 1795 represent equipotential lines of the reflected wave, at the first carrier frequency. Dashed lines 1797 represent equipotential lines of the incident wave, and dashed lines 1798 represent equipotential lines of the reflected wave, at the second carrier frequency. Solid dots 1796 represent the nulls at the first frequency. Hollow dots 1799 represent the nulls at the second frequency. The acoustic signal is received by implantable medical device 120 when the acoustic transducer does not coincide with nulls at both frequencies, i.e., does not coincide with both one of solid dots 1796 and one of hollow dots 1799. Three or more carrier frequencies may be used for the frequency diversity to further ensure reliability of the acoustic communication. In one embodiment, two carrier frequencies are considered sufficient because the chance that the nulls at two substantially different frequencies coincide is considered as being sufficiently small.

In one embodiment, when the error rate of the incoming date exceeds the predetermined threshold rate, as determined by error detector 1676, frequency selection circuit 1678 selects a substantially different frequency to be the carrier frequency for the acoustic communication. For example, acoustic communication circuit 1630 uses first and second carrier frequencies for the acoustic communication via acoustic couple 115. When acoustic couple 115 is established or activated, frequency selection circuit 1678 selects the first carrier frequency. When error detector 1676 detects an intolerable error rate, frequency selection circuit 1678 selects the second carrier frequency to replace the first carrier frequency. When error detector 1676 detects another intolerable error rate, with the second carrier frequency, frequency selection circuit 1678 selects the first carrier frequency to replace the second carrier frequency. In this embodiment, carrier generator 1660 includes a variable-frequency carrier generator that generates the carrier signal at the frequency selected by frequency selection circuit 1678. In one specific embodiment, the first carrier frequency is 39 kHz, and the second carrier frequency is 43 kHz. In one embodiment, the acoustic transducer has a low quality factor (Q). Components of acoustic communication circuit 1630, except carrier generator 1662, need no adjustment when the carrier frequency changes from the first carrier frequency to the second carrier frequency. In one embodiment, acoustic communication circuit 1630 has two frequency bands each accommodate one of the carrier frequencies. In another embodiment, acoustic communication circuit 1630 has one wide frequency band that accommodates both carrier frequencies.

In one embodiment, frequency diversity is employed to allow implantable medical device 110 to communicate with two or more other implantable medical devices via separate acoustic couples each using a substantially distinctive carrier frequency. This allows simultaneous communications via multiple acoustic couples.

Figure 18:
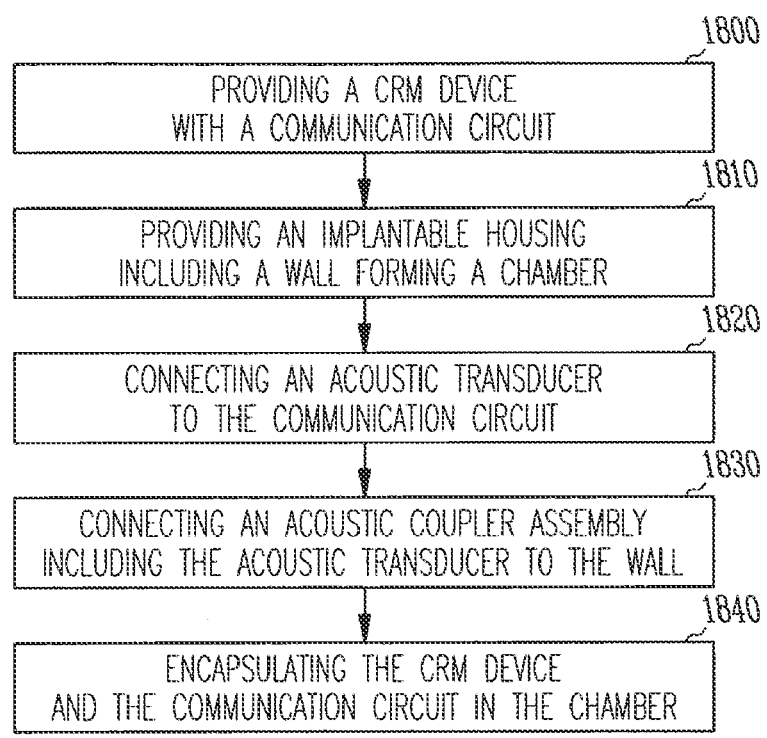
FIG. 18 is a flow chart illustrating an embodiment of a method for making an implantable medical device with an acoustic transducer for acoustic communication.

FIG. 18 is a flow chart illustrating an embodiment of a method for making an implantable medical device with an acoustic transducer for acoustic communication. In one embodiment, the method is applied to make implantable medical device 110 with acoustic transducers 232 including, but not being limited to, all the embodiments discussed in this document.

A CRM device with a communications circuit is provided at 1800. The CRM device includes, but is not limited to, one or more of a monitoring device sensing one or more types of physiologic signals, a pacing device, a cardioversion/defibrillation device, a CRT device, a RCT device, a drug delivery device, a cell therapy device, a gene therapy device, and a therapy delivery controller device.

An implantable housing is provided at 1810. The implantable housing includes a wall forming a chamber. In one embodiment, the implantable housing is made of a biocompatible metal such as titanium.

An acoustic transducer is connected to the communication circuit of the CRM device at 1820. The acoustic transducer functions as an acoustic coupler for the acoustic communication. In one embodiment, a single piezoelectric transducer is connected to the communication circuit. In another embodiment, a piezoelectric transducer array including two or more piezoelectric transducers is connected to the communication circuit. In one embodiment, programmable interconnections are provided for the two or more piezoelectric transducers, such that the interconnections among the piezoelectric transducers can be changed to provide an electronically adjustable overall impedance. In one embodiment, a transducer interface circuit is provided to control a directionality of the acoustic transducer functioning as the acoustic coupler.

An acoustic coupler assembly including the acoustic transducer is connected to the wall of the implantable housing at 1830. In one embodiment, the acoustic coupler assembly includes essentially the acoustic transducer. In another embodiment, the acoustic coupler assembly further includes supporting or other structure such as diaphragm 645 and 945 discussed above. The acoustic coupler assembly is fastened to the wall of the implantable housing. In one embodiment, the acoustic coupler assembly is glued to the wall of the implantable housing. In another embodiment, the acoustic coupler assembly is welded to the wall of the implantable housing. In another embodiment, the acoustic coupler assembly is soldered to the wall of the implantable housing. In another embodiment, the acoustic coupler assembly is braced to the wall of the implantable housing. In another embodiment, a portion of the wall of the implantable housing is thinned, and the acoustic coupler assembly is fastened to the thinned portion of the wall. In one embodiment, the acoustic coupler assembly is fastened to the interior surface of the wall, which is on the side of the chamber formed by the wall. In another embodiment, the acoustic coupler assembly is fastened to the exterior surface of the wall. In one embodiment, the acoustic coupler assembly includes a diaphragm, and the acoustic transducer is fastened to the diaphragm, which is connected to the wall. In one specific embodiment, the diaphragm is connected to the exterior surface of the wall to form an isolated cavity between the diaphragm and the exterior surface, and the acoustic transducer is fastened to the surface of the diaphragm within the cavity. In another specific embodiment, the wall of the implantable housing includes a hole, and the diaphragm is connected to the wall to cover the hole. In one embodiment, the acoustic transducer is an acoustic transducer array including the two or more piezoelectric transducers physically stacked together and fastened to the wall of the implantable housing. In another specific embodiment, the acoustic transducer is an acoustic transducer array including the two or more piezoelectric transducers, with each piezoelectric transducer of the piezoelectric transducer array fastened to the wall.

The CRM device and the communication circuit are encapsulated in the chamber of the implantable housing to form an implantable medical device at 1840. The chamber is hermetically sealed for implantation.

It is to be understood that the above detailed description is intended to be illustrative, and not restrictive. As discussed above, while a CRM system is used as a specific example, the present subject matter generally provides for intra-body communication for any type of implantable medical device. Such implantable medical device includes diagnostic and therapeutic devices such as any patient monitoring devices, neural stimulators, neuromuscular stimulators, and any drug delivery systems. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system for acoustically communicating with multiple implantable medical devices, the system comprising:
    an implantable medical device including an acoustic communication circuit and at least one acoustic transducer configured for acoustically communicating with a plurality of remote devices;
    the acoustic communication circuit including:
        a data transmitter circuit including a carrier generator adapted to modulate and transmit an outgoing acoustic signal to each remote device, the outgoing acoustic signal transmitted to each remote device including a carrier signal having a distinct carrier frequency;
        a data receiver circuit adapted to receive and demodulate an incoming acoustic signal from each remote device; and
        a frequency selection circuit configured for adjusting the carrier frequency of the outgoing acoustic signal transmitted to each remote device.

2. The system of claim 1, wherein the carrier generator comprises a variable-frequency waveform generator.

3. The system of claim 1, wherein the data receiver circuit includes an error detector configured for detecting an error rate associated with each demodulated incoming acoustic signal.

4. The system of claim 3, wherein the frequency selection circuit is configured to adjust the carrier frequency of each outgoing acoustic signal in response to the error rate associated with each demodulated incoming acoustic signal.

5. The system of claim 4, wherein the frequency selection circuit is configured to select the carrier frequency of each outgoing acoustic signal based on a comparison of the error rate of each demodulated incoming acoustic signal to a threshold error rate.

6. The system of claim 1, wherein the acoustic communication circuit further comprises a transducer interface circuit including a tuning circuit.

7. The system of claim 6, wherein the tuning circuit includes impedance matching or impedance control circuitry.

8. The system of claim 6, wherein the at least one acoustic transducer comprises a plurality of acoustic transducer elements, and wherein the tuning circuit includes a steering circuit configured to control the transducer elements.

9. The system of claim 1, wherein the plurality of remote devices comprises at least one monitoring device.

10. The system of claim 1, wherein the plurality of remote devices comprises at least one therapy delivery device.

11. The system of claim 1, further comprising a wireless telemetry link between the implantable medical device and an external device located outside of the body.

12. An implantable medical device, comprising:
- at least one acoustic transducer;
- an acoustic communication circuit coupled to the at least one transducer, the acoustic communication circuit comprising a data transmitter circuit including a carrier generator adapted to modulate and transmit a plurality of outbound acoustic signals each at a distinct carrier frequency;
- a data receiver circuit configured to receive and modulate incoming acoustic signals;
- an error detection circuit configured for detecting an error rate associated with the demodulated incoming acoustic signals; and
- a frequency selection circuit configured for adjusting the carrier frequency of each outbound acoustic signal based at least in part on the error rate.

13. The device of claim 12, wherein the frequency selection circuit is configured to select the carrier frequency of each outgoing acoustic signal based on a comparison of the error rate of each demodulated incoming acoustic signal to a threshold error rate.

14. The device of claim 12, wherein the acoustic communication circuit further comprises a transducer interface circuit including a tuning circuit.

15. The device of claim 14, wherein the tuning circuit includes impedance matching or impedance control circuitry.

16. The device of claim 14, wherein the at least one acoustic transducer comprises a plurality of acoustic transducer elements, and wherein the tuning circuit includes a steering circuit configured to control the transducer elements.

17. A method of acoustically communicating with multiple implantable medical devices, comprising:
- transmitting a first outgoing acoustic signal from an acoustic transducer of an implantable medical device to a first remote device and establishing a first acoustic coupling within a body, the first outgoing acoustic signal including a first carrier frequency;
- transmitting a second outgoing acoustic signal from the acoustic transducer of the implantable medical device to a second remote device and establishing a second acoustic coupling within the body, the second outgoing acoustic signal including a second carrier frequency distinct from the first carrier frequency;
- receiving and demodulating an incoming acoustic signal from at least one of the first and second remote devices; and
- adjusting at least one of the first and second carrier frequencies of the outgoing acoustic signal.

18. The method of claim 17, further comprising:
- detecting an error rate associated with each demodulated incoming acoustic signal; and
- adjusting at least one of the first and second carrier frequencies of the outgoing acoustic signals based on the error rate.

19. The method of claim 17, wherein adjusting at least one of the first and second carrier frequencies includes comparing the error rate associated with each demodulated incoming acoustic signal to a predetermined threshold error rate for each acoustic coupling.

20. The method of claim 17, wherein the acoustic transducer comprises a plurality of transducer elements, and further comprising a means for controlling the transducer elements to steer the first and second outgoing acoustic signals.

* * * * *